United States Patent
Geskin et al.

(10) Patent No.: US 9,655,950 B2
(45) Date of Patent: May 23, 2017

(54) ACTIVATION OF MYELOID-DERIVED SUPPRESSOR CELLS AS A PREDICTOR OF PATIENT RESPONSE TO INTERFERON-A THERAPY

(71) Applicant: University of Pittsburgh—of the Commonwealth System of Higher Education, Pittsburgh, PA (US)

(72) Inventors: Larisa Geskin, Pittsburgh, PA (US); Oleg E. Akilov, Pittsburgh, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 0 days.

(21) Appl. No.: 14/535,198

(22) Filed: Nov. 6, 2014

(65) Prior Publication Data

US 2015/0064136 A1    Mar. 5, 2015

Related U.S. Application Data

(63) Continuation of application No. PCT/US2013/040161, filed on May 8, 2013.

(60) Provisional application No. 61/644,300, filed on May 8, 2012.

(51) Int. Cl.
| | |
|---|---|
| *A61K 38/21* | (2006.01) |
| *G01N 33/50* | (2006.01) |
| *G01N 33/574* | (2006.01) |
| *G01N 33/84* | (2006.01) |

(52) U.S. Cl.
CPC ........ *A61K 38/212* (2013.01); *G01N 33/5011* (2013.01); *G01N 33/57407* (2013.01); *G01N 33/84* (2013.01); *G01N 2333/4706* (2013.01); *G01N 2333/90* (2013.01); *G01N 2333/978* (2013.01); *G01N 2800/52* (2013.01)

(58) Field of Classification Search
None
See application file for complete search history.

(56) References Cited

U.S. PATENT DOCUMENTS

2012/0070461 A1    3/2012 Singh et al.

OTHER PUBLICATIONS

Cai et al., "Clinical Significance and Functional Studies of Myeloid-Derived Suppressor Cells in Chronic Hepatitis C Patients" *J Clin Immunol* 33:798-808, 2013.

Corzo et al., "Mechanism regulating reactive oxygen species in tumor-induced myeloid-derived suppressor cells" *J Immunol* 182:5693-701, 2009.
Dillman, "Cancer Immunotherapy" *Cancer Biotherapy & Radiopharmaceuticals*, vol. 26, No. 1, pp. 1-64 (2011).
International Search Report dated Aug. 6, 2013 in International Application No. PCT/US2013/040161.
Le et al., "Gemcitabine directly inhibits myeloid derived suppressor cells in BALB/c mice bearing 4T1 mammary carcinoma and augments expansion of T cells from tumor-bearing mice" *Int Immunopharmacol* 9:900-909, 2009.
Norris et al., "Chronic but Not Acute Virus Infection Induces Sustained Expansion of Myeloid Suppressor Cell Numbers that Inhibit Viral-Specific T Cell Immunity" *Immunity* 38:309-21, 2013.
Ochoa et al., "Arginase, Prostaglandins, and Myeloid-Derived Suppressor Cells in Renal Cell Carcinoma" *Clinical Cancer Research*, vol. 13, No. Suppl. 2, pp. 721s-726s (2007).
Poehlein et al., "Depletion of tumor-induced regulatory T cells prior to reconstitution rescues enhanced priming of tumor-specific, therapeutic effector T cells in lymphopenic hosts" *Eur J Immunol* 39:3121-3133, 2009.
Porta et al., "Cellular and molecular pathways linking inflammation and cancer" *Immunobiology*, vol. 214, No. 9, pp. 761-777 (2009).
Poschke et al., "Immature Immunosuppressive CD14+ HLA-DR-/Low Cells in Melanoma Patients Are Stat3hi and Overexpress CD80, CD83, and DC-Sign" *Cancer Research*, vol. 70, No. 11, pp. 4335-4345 (2010).
Sinha et al., "Reduction of Myeloid-Derived Suppressor Cells and Induction of M1 Macrophages Facilitate the Rejection of Established Metastatic Disease" *J Immunol* 174:636-45, 2005.
Steding et al., "The role of interleukin-12 on modulating myeloid-derived suppressor cells, increasing overall survival and reducing metastasis" *Immunology* 133:221-238.
Vasievich, et al., "The Suppressive Tumor Microenvironment: A Challenge in Cancer Immunotherapy" *Mol Pharm* 8:635-41, 2011.
Youn et al., "The biology of myeloid-derived suppressor cells: the blessing and the curse of morphological and functional heterogeneity" *Eur J Immunol* 40:2969-75, 2011.
Zoglmeier et al., "Cpg Blocks Immunosuppression by Myeloid-Derived Suppressor Cells in Tumor-Bearing Mice" *Clin Cancer Res* 17:1765-75, 2011.

*Primary Examiner* — Christine J Saoud
*Assistant Examiner* — Jegatheesan Seharaseyon
(74) *Attorney, Agent, or Firm* — Baker Botts L.L.P.

(57) ABSTRACT

The present invention relates to methods and materials for more effectively treating patients with interferon. It is based on the discovery that clinical response to interferon (IFN) therapy is mediated in part by inhibition of activation of MDSC and such inhibition can be observed after a test dose of interferon; a significant decrease of reactive oxygen species (ROS) production by MDSC (as a measure of their activation) after IFN therapy is predictive of overall response to immunotherapy in cancer patients.

7 Claims, 8 Drawing Sheets

RESPONDER

FIG. 3A

NON-RESPONDER

FIG. 3B

ACTIVATION OF MYELOID-DERIVED SUPPRESSOR CELLS AS A PREDICTOR OF PATIENT RESPONSE TO INTERFERON-A THERAPY

PRIORITY CLAIM

This application is a continuation of International Application No. PCT/US2013/040161 filed May 8, 2013, now published as International Publication No. WO 2013/169913 A1, which claims priority to U.S. Provisional Application No. 61/644,300 filed May 8, 2012, the contents of which are incorporated by reference in their entireties herein, and to each of which priority is claimed.

GRANT INFORMATION

This invention was made with government support under Grant No. CA121973 awarded by the National Institutes of Health. The government has certain rights to the invention.

1. INTRODUCTION

The present invention relates to interferon therapy. In certain embodiments, significant decrease in functional activation of myeloid-derived suppressor cells after a test dose of interferon predicts effective clinical responses to the full course of interferon-α therapy in patients treated with interferon for cancers and for chronic viral infections.

2. BACKGROUND OF THE INVENTION

Myeloid-derived suppressor cells (MDSC) play a crucial role in inhibiting anticancer defenses, resulting in tumor escape from immunologic surveillance, progressive cancer growth and metastasis. MDSC are a heterogeneous group of leucocytes present in the circulation, lymphoid compartments and infiltrating human cancers inhibiting cell-mediated immune functions[1]. Immunotherapeutic strategies capable of inhibiting or deleting MDSC are desirable to enhance antitumor immune response.

MDSC have recently been shown to be involved in chronic viral illnesses[2,3]. Several chronic viral infections such as chronic viral hepatitis C, are known to respond to interferon, but again, such response in these patients is not universal even within a specific genotype and predictors of clinical response in these patients are necessary.

Interferons (IFN) are common therapies used for various medical conditions, including melanoma, lymphoma, hepatitis and many others. However, currently, there are no specific biomarkers to distinguish which patient population would respond to the therapy with IFN. As a result, all patients receive this toxic therapy on a trial-and-error basis without knowing a priori whether they would benefit from it or not.

According to a comprehensive report "Interferon Market Forecast to 2015" dated Nov. 2, 2012 (marketandreports.wordpress.com), the consumption of the interferon drugs is increasing, and is expected to cross the $10 billion-mark by 2015. Increasingly, in light of shrinking healthcare dollars, insurance companies begin to demand significant supporting evidence for inclusion of drugs into formularies and verification of their cost-effectiveness. In the future, therapeutic choices will be limited even more by these restrains. It would be of great benefit to have a standard test predictive of a response to IFN, to increase cost-benefit ratio and to provide valuable therapy to those who would benefit from it the most, while sparing others from undesirable toxicity and unnecessary financial losses.

3. SUMMARY OF THE INVENTION

The present invention relates to methods and materials for more effectively treating patients with interferon. It is based on the discovery that clinical response to interferon (IFN) therapy is mediated in part by inhibition of activation of MDSC and such inhibition can be observed after a test dose of interferon; a significant decrease of one or more activation markers such as reactive oxygen species (ROS) production, intracellular pSTAT3 and/or serum arginase 1 after IFN therapy is predictive of overall response to immunotherapy in cancer patients.

In certain non-limiting embodiments, activation of myeloid-derived suppressor cells is used to predict whether IFN therapy is likely to be effective, where an elevated activation level indicates a greater likelihood that IFN therapy will be effective. Effectiveness in treatment of cancer and viral infection is contemplated.

In certain embodiments of the invention, the clinical response to IFN therapy can be predicted and appropriate patients may be selected for further therapy based on a test comprising pairing up levels of ROS produced by MDSC before and after a test dose of IFN such that the patients who will benefit from IFN the most can be selected and treated with the entire course of therapy, because of positive risk-benefit ratio. In certain specific non-limiting embodiments, functional suppression of the myeloid-derived suppressor cells after a single test dose of IFN-α is used to predict whether IFN-α is likely to be effective.

4. BRIEF DESCRIPTION OF THE FIGURES

FIGS. 2A-1-2E. Characterization of MDSC in cutaneous T cell lymphoma ("CTCL") patients and healthy volunteers. 2A-1. Characterization of MDSC population. Granulocytic MDSC were determined as cells with CD33+CD14−CD11b+HLA-DR−CD86+phenotype. 2A-2. Representative flow of percentage of MDSC among CD11b in healthy volunteers or patients with CTCL. 2B-1. Absolute number of MDSC in peripheral blood of controls and patients with LTB, HTB or SzS. *,p<0.01. 2B-2. ROS production by MDSC in patients with controls, LTB, and HTB. *,p<0.01. 2C-2E. Representative histogram for ROS production by MDSC; dotted-isostype; solid-control, dashed-LTB, and tinted-HTB.

FIGS. 4A-4C. Efficacy of therapy with INF-$\alpha_{2b}$ is mediated via reduction of ROS production by MDSC in patients with CTCL. A. The absolute number of MDSC in peripheral blood of patients before and after IFN-$\alpha_{2b}$ (5 patients). B. Response to IFN-α2b is associated with decrease in ROS production by MDSC activation. R—Responder;

NR—Non-Responder. C. Response to IFN-α2b is associated with decrease in serum arginase. R—Responder; NR—Non-Responder

5. DETAILED DESCRIPTION OF THE INVENTION

In certain non-limiting embodiments, the present invention provides for a method of determining whether interferon-α is likely to be therapeutically effective in a subject suffering from a cancer or viral infection comprising determining whether the activation level of myeloid-derived suppressor cells of the subject is reduced in response to treatment with interferon-α, where if the activation level of myeloid-derived suppressor cells is reduced the subject has a greater likelihood of benefiting from further interferon-α therapy. In one particular non-limiting embodiment, the subject is suffering from cutaneous T-cell lymphoma (CTCL). In certain non-limiting embodiments a reduced activation level is indicated by reduced MDSC production of ROS, reduced MDSC intracellular pSTAT3 and/or reduced serum arginase 1, all markers of MDSC activation as discussed below.

In certain non-limiting embodiments, the present invention provides for a method of determining whether IFN-α is likely to be therapeutically effective in a subject suffering from a cancer or viral infection (also referred to herein as a "patient") comprising determining whether a reduction in ROS production by MDSC of the subject is observed in response to a test dose of IFN-α, where if the ROS production by MDSC is significantly suppressed the subject has a greater likelihood of benefiting from full course of IFN-α therapy. The test dose may, in non-limiting embodiments, be a single test dose. In one particular non-limiting embodiment, the subject is suffering from CTCL.

In related non-limiting embodiments, the ability of IFN-α to reduce the activation level of MDSC, for example as determined using a marker of MDSC activity, may be evaluated in vitro, for example in a cell culture containing an enriched population of MDSC from a subject suffering from a cancer or viral infection, where IFN-α is added to the culture to approximate the concentration attained in vivo, and then the effect of IFN-α on MDSC activation is evaluated and a reduction in MDSC activation is indicative that the subject would benefit from IFN-α treatment. In a specific non-limiting embodiment, the effect may be measured using intraceullar MDSC ROS production, whereby a reduction in ROS production indicates that the subject may benefit from IFN-α therapy.

In certain non-limiting embodiments, the present invention provides for a method of treating a subject suffering from cancer or viral infection comprising (i) evaluating the likelihood of IFN-α to be therapeutically effective by determining the baseline level of ROS production by MDSC in the patient relative to a normal control, where the higher ROS production by MDSC the greater is the likelihood of benefiting from IFN-α therapy; and (ii) if there is a significant reduction in the ROS production by MDSC after a single test dose of IFN-α, then treating the subject with IFN-α will be beneficial and should be continued. This method may be of particular benefit to subjects with advanced cancer due to the higher state of MDSC activation in these patients. In one particular non-limiting embodiment, the subject is suffering from CTCL.

In certain non-limiting embodiments, the present invention provides for a method of determining whether IFN-α is likely to be therapeutically effective in a subject suffering from a cancer or viral infection (also referred to herein as the "patient") comprising determining whether the activation level of MDSC in the subject is elevated relative to a normal control value, where if the activation level is elevated the subject has a greater likelihood of benefiting from IFN-α therapy. In a specific non-limiting embodiment, the cancer is CTCL.

In certain non-limiting embodiments, the present invention provides for a method treating a subject suffering from a cancer or viral infection, comprising (i) determining whether IFN-α is likely to be therapeutically effective in the patient by determining whether the activation level of MDSC in the patient is elevated relative to a normal control value, where if the activation level is elevated the patient has a greater likelihood of benefiting from IFN-α therapy; and (ii) if the activation level of MDSC is elevated relative to a normal control value, then treating the subject with IFN-α. This method may be of particular benefit to subjects who have not yet been treated with IFN-α but it may also be applied to patients who have received such therapy.

The subject is a human subject.

In addition to CTCL, other cancers to which the invention may be applied include other types of cancer in which IFN-α is a treatment used in the art, including but not limited to melanoma, lymphoma and Kaposi's sarcoma.

Viral infections to which the invention may be applied include viral infections in which IFN-α treatment is known in the art, including but not limited to hepatitis, such as hepatitis B, C and D. In certain non-limiting embodiments the viral infection is a chronic infection.

"Therapeutically effective" or therapeutic benefit mean providing a clinical and pathological benefit, for example one or more of reducing the number of skin lesions, reducing tumor burden, reducing patient's pain, reducing patient's discomfort, or prolonging survival. In the working examples below, patients receiving a therapeutic benefit are referred to as "responders" and patients that did not receive a therapeutic benefit are referred to as "non-responders".

MDSC cells for study may be obtained from peripheral blood of cancer patients.

An elevated activation level relative to a normal control value is an activation level which is at least about 150 percent or at least about 180 percent of a normal control value. In a particular non-limiting embodiment, an elevated level of ROS produced by MDSC relative to a normal control value is a level which is at least 2 times greater than a normal control value.

A reduction in activation level, for example as reflected in reduction of an activation marker, may be at least a 30 percent reduction relative to the initial level or value. For example, reduction in ROS production by MDSC after a test dose of IFN-α may be a reduction by at least 30 percent from the initial value.

A normal control value may be the ROS level measured in a normal control subject or an average or mean value among a plurality of normal control subjects. It may be established in an assay run in parallel to that of the patient being evaluated or treated, or it may be separately determined.

Markers of MDSC activation include, but are not limited to intracellular ROS, serum arginase-1, and intracellular STAT5, all of which increase with increased MDSC activation. One or more marker of MDSC activation may be used in various embodiments of the invention. For clarity by example but not by way of limitation, an elevation in the intracellular MDSC level of ROS which is 2 times of a normal control intracellular MDSC level indicates an elevated level of functional activity. Reduction of one or more of MDSC ROS, MDSC pSTAT3 and/or serum Arg1 are indicative in a decrease in activation in response to IFN-α therapy.

For measuring intracellular ROS values in MDSC, it is desirable to study a population of cells enriched for MDSC, for example but not limited to essentially isolated or isolated MDSC. As that term is used herein, MDSC are cells having the surface markers CD33(+)CD11b(+)CD86(+)CD14(−)HLA-DR(−). Cells having this phenotype may be collected using methods known in the art, for example, but not limited to, flow cytometry or fluorescence activated cell sorting ("FACS") using antibodies directed to the above markers. Methods for collecting MDSC are described in the working examples below.

Measurement of intracellular MDSC ROS levels may be performed using methods known in the art. In a particular non-limiting embodiment, cells may be suspended at $1.5 \times 10^6$ cells per 100 µl in pre-warmed Hank's buffer containing 2% FBS, and 1 µM 6-carboxy-2',7'-dichlorodihydrofluorescein diacetate, di(acetoxymethyl ester) (carboxyl-DCFH-DA) (Invitrogen, Carlsbad, Calif.) may be added to the cell suspension with subsequent incubation at 37° C. for 30 min. Washed cells may then be resuspended in flow buffer and fluorescence emitted in 535 nm was read after excitation at 485 nm. Cells stimulated with 3% $H_2O_2$ may be used as positive control. A variety of techniques can be used to detect this fluorescence: FACS, fluorescence microscopy of MDSC population collected via magnetic bead isolation. Alternative means for measuring ROS could be colorimetric assay such as nitroblue tetrazolium and diaminobenzidine tetrahydrochloride methods.

Measurement of intracellular MDSC pSTAT3 may be performed using methods known in the art. For example, but not by way of limitation, intracellular pSTAT3 may be measured by flow cytometry or fluorescence activated cell sorting ("FACS") using antibodies directed to the above markers.

Measurement of serum arginase-1 may be performed using methods known in the art. For example, arginase-1 may be measured by an antibody-mediated assay such as Western blot or enzyme linked immunosorbent assay ("ELISA"). Alternatively arginase-1 may be measured by determining arginase enzyme activity.

IFN-α" as that term is used herein refers to interferon-α2b, interferon-α2a, and pegylated versions thereof, for example molecules sold under the tradenames INTRON-A® (interferon-α2b), PEGINTRON® (peginterferon α-2b), ROFERON-A® (interferon α-2a) and PEGASYS® (peginterferon α-2a).

Treating the subject with IFN-α" means: administering a therapeutically appropriate dose of IFN-α to a subject per standard of care. For example, but not by way of limitation, interferon α2b may be provided to a subject as sold under the commercial name INTRON-A® (interferon-α2b) at a dose 5, 10, or 15 million international units (IU) three times a week or as pegylated interferon α (e.g. sold under the commercial name PEGINTRON® (peginterferon α-2b) at a dose of 1.25 µg/kg weekly). Interferon treatment as referred to herein may be administered via any appropriate route including but not limited to subcutaneous, intramuscular, intravenous, etc.

In certain non-limiting embodiments, the invention provides a kit for measuring MDSC activity. In particular non-limiting embodiments, said kit may comprise (i) material for enriching or isolating a plurality of MDSC and/or (ii) material for measuring ROS production or another marker of MDSC activation. Non-limiting examples of material for enriching or isolating a plurality of MDSC include one or more detection means for a surface marker of a MDSC cell, for example an immunoglobulin or immunoglobulin fragment that specifically binds to CD33, CD11b, CD86, CD14, or HLA-DR. Non-limiting examples of material for measuring one or more marker of MDSC activation include one or more of 6-carboxy-2',7'-dichlorodihydrofluorescein diacetate, di(acetoxymethyl ester) (carboxyl-DCFH-DA), nitroblue tetrazolium, diaminobenzidine tetrahydrochloride, an immunoglobulin or immunoglobulin fragment that binds to Arg1, and/or an immunoglobulin or immunoglobulin fragment that binds to pSTAT3. Optionally an immunoglobulin or immunoglobulin fragment may be detectably labeled. Optionally a kit may further comprise a secondary antibody which binds to one of the recited immunoglobulins or immunoglobulin fragments.

Of note, any of the therapeutic regimens described herein, in this or other sections, may be combined with other forms of therapy, including but not limited to treatment with bexarotene, 13-cis-retinoic acid, photochemotherapy, histone deacetylase inhibitors, small molecules, or other biologic and chemotherapy.

6. EXAMPLE: FUNCTIONAL REDUCTION OF MYELOID-DERIVED SUPPRESSOR CELL ACTIVATION IS ASSOCIATED WITH RESPONSE TO PEGYLATED INTERFERON-A2B THERAPY IN PATIENTS WITH CUTANEOUS T-CELL LYMPHOMA

6.1 Materials and Methods

Patients and Healthy Volunteers

The study protocol was approved by the Institutional Review Board of the University of Pittsburgh Medical Center in Pittsburgh, Pa. This study was registered through www.clinicaltrials.gov [NCT00254332].

Figure 1:
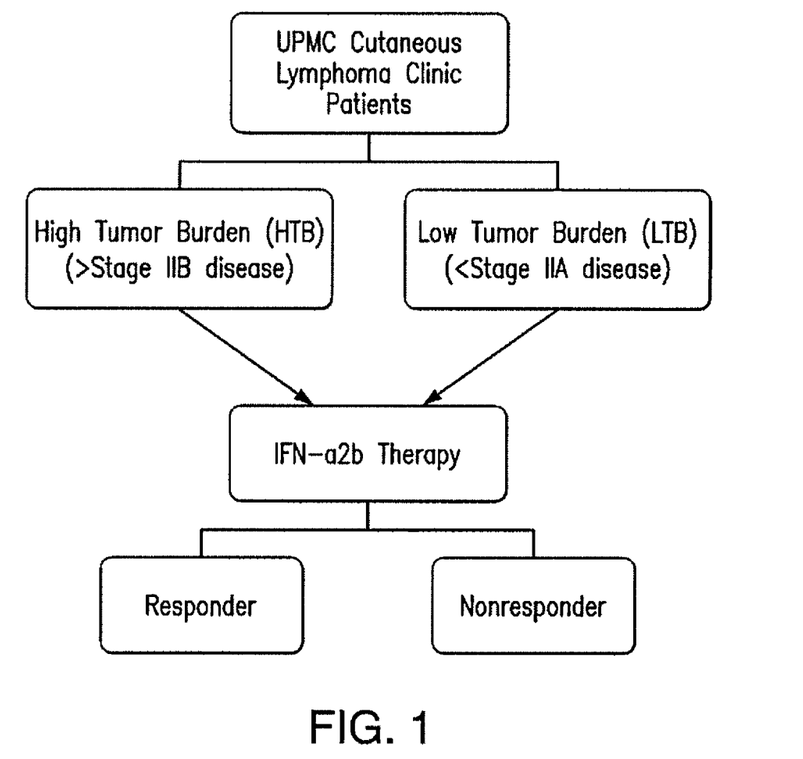
FIG. 1. Flow chart depicting patient categories.

Patients under our direct care were seen at the Cutaneous Lymphoma Clinic at the University of Pittsburgh were enrolled in the study. Peripheral blood samples were collected for research purposes only if blood draw was medically indicated. The patients were separated into two distinct categories (FIG. 1): Group 1, low tumor burden (LTB), when only minor skin involvement present (<5% patches); Group 2, high tumor burden (HTB) patients with significant skin involvement of at least 20% of TBSA (correspond to stage IB and above) with numerous tumors and/or ulcers, extensive plaques or erythroderma.

A total of 22 patients who were candidates for IFN-$α_{2b}$ therapy were invited to participate in the study. Patients who consented to blood draws for research purposes before and during IFN therapy were enrolled in the study. Patients were followed up as clinically appropriate and clinical assessment was performed during each clinic visit.

Flow Cytometry

PBMC from peripheral blood (at least 15 ml of blood collected and processed within 2-4 hours) were isolated with Ficoll-Paque gradient according to manufacturer's instruction (*Amersham Biosciences*), washed twice with PBS, and incubated with 10% normal serum to block unspecific binding before staining. The following markers were used for MDSC: anti-CD33-PE-Cy5 (WM53), anti-CD14-FITC (M5E2), anti-CD11b-APC (ICRF44), anti-CD86-PE (FUN- 1) from BD Pharmingen (San Diego, Calif.); and anti-HLA-DR-Pacific Blue (L243) from BioLegend (San Diego, Calif.). The cells were evaluated using FACSAria and CellQuest Software (Becton Dickenson, San Jose, Calif.). The absolute numbers were calculated based on the commercial complete blood count data drawn on the same day. FlowJo software (Tree Star Inc, Ashland, Oreg.) was used for analysis of flow cytometric data.

Assessment of Intracellular ROS

Cells were washed out of culture medium and left for 10 min in PBS, resuspended at $1.5 \times 10^6$ 100 μl in pre-warmed Hank's buffer containing 2% FBS. 1 μM 6-carboxy-2',7'-dichlorodihydrofluorescein diacetate, di(acetoxymethyl ester) (carboxyl-DCFH-DA) (Invitrogen, Carlsbad, Calif.) was added to the cell suspension with subsequent incubation at 37° C. for 30 min. Washed cells were resuspended in flow buffer and fluorescence emitted in 535 nm was read after excitation at 485 nm. Cells stimulated with 3% $H_2O_2$ were used as positive control.

Statistical Analysis

The statistical analysis was based on the calculation of arithmetic mean and standard deviation. The difference between two means was compared by a two-tailed unpaired Student's t test without assumption of equal variances. The relationship between two or more variables was measured by correlation analysis (Pearson coefficient). A p-value of less than 0.05 was considered statistically significant.

6.2 Results

Reduction of MDSC activity is a promising adjuvant to immunotherapeutic agents[4]. The inhibition of MDSC suppressive function has been correlated with significant reductions in tumor spread even in cases where local tumor growth was not altered. While therapy with DD did not affect the absolute number of MDSC, we investigated whether the benefit of IFN-α2b therapy in patients with CTCL is mediated by alternation of the number and/or functions of MDSC. Previous investigation in murine model demonstrated that IFN-α is capable of inhibiting suppressive effect of MDSC via induction of maturation and differentiation of MDSC[6].

Figure 2A:
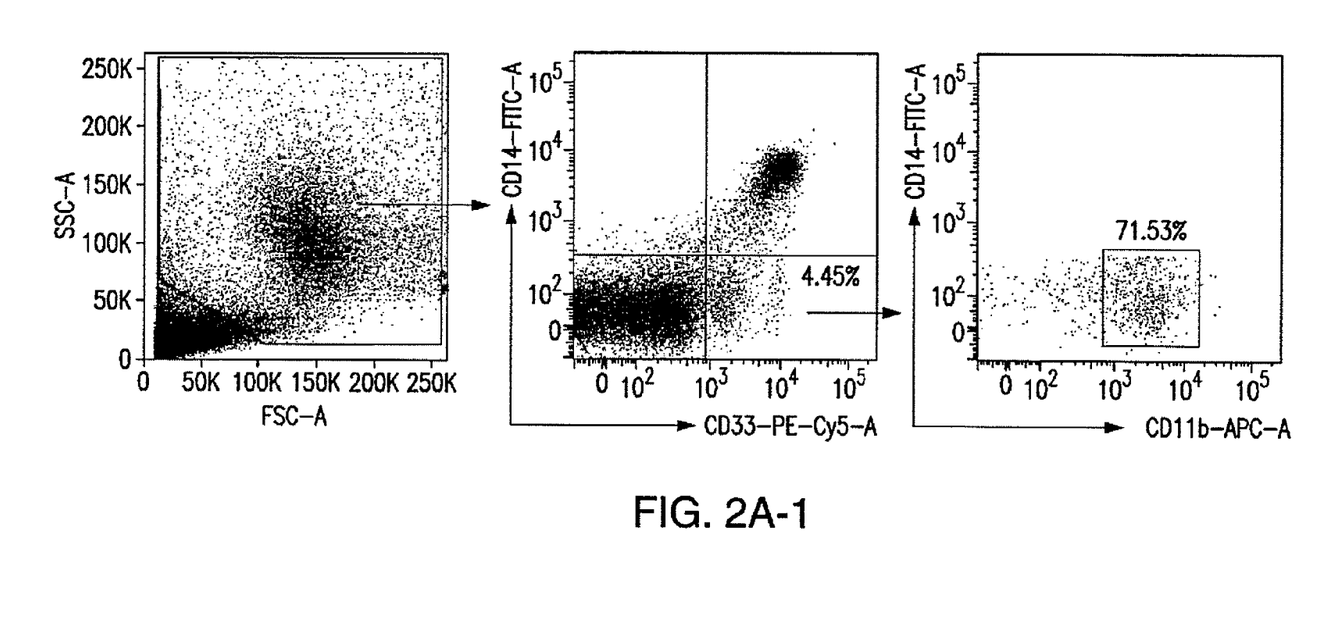
Figure 2A:
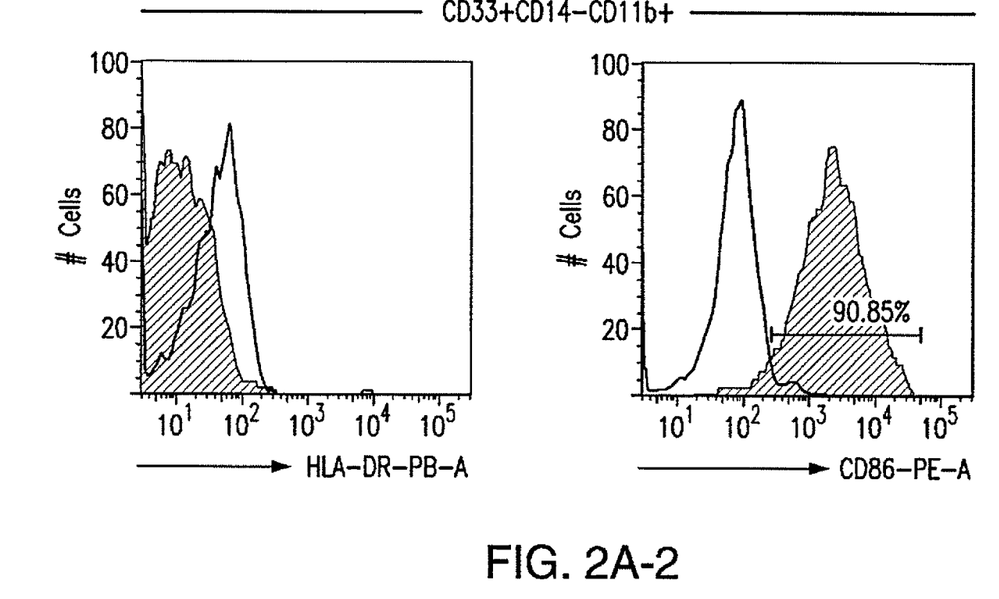
Figure 2B:
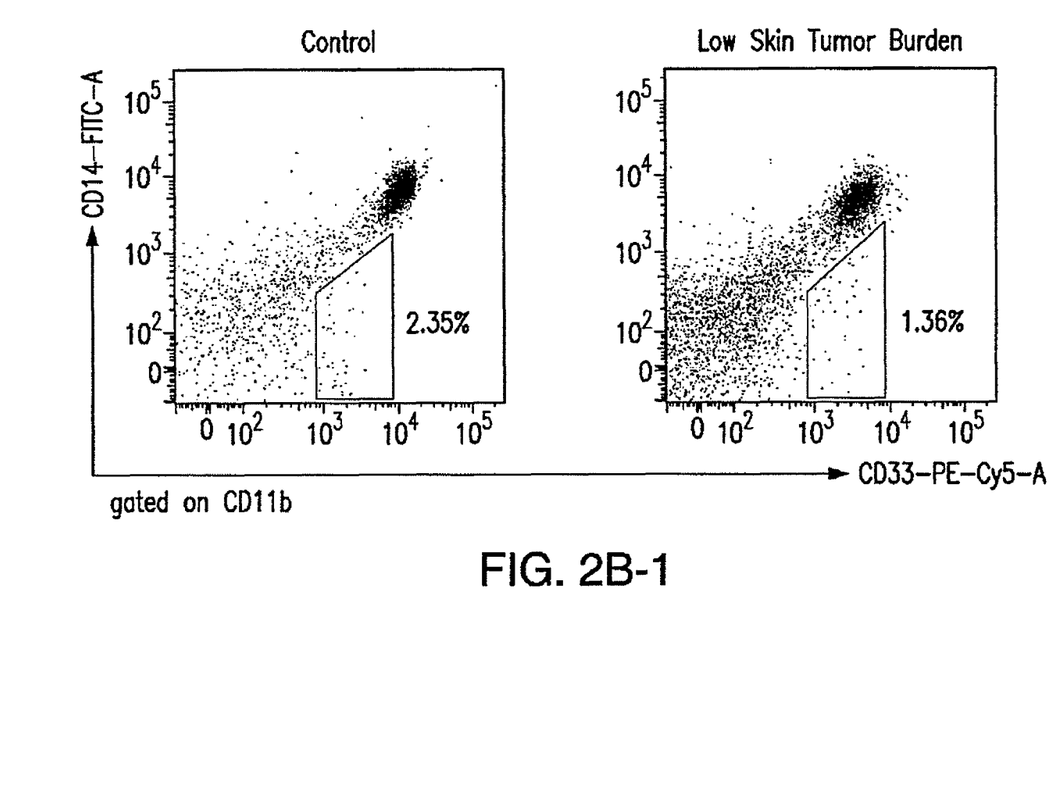
Figure 2B:
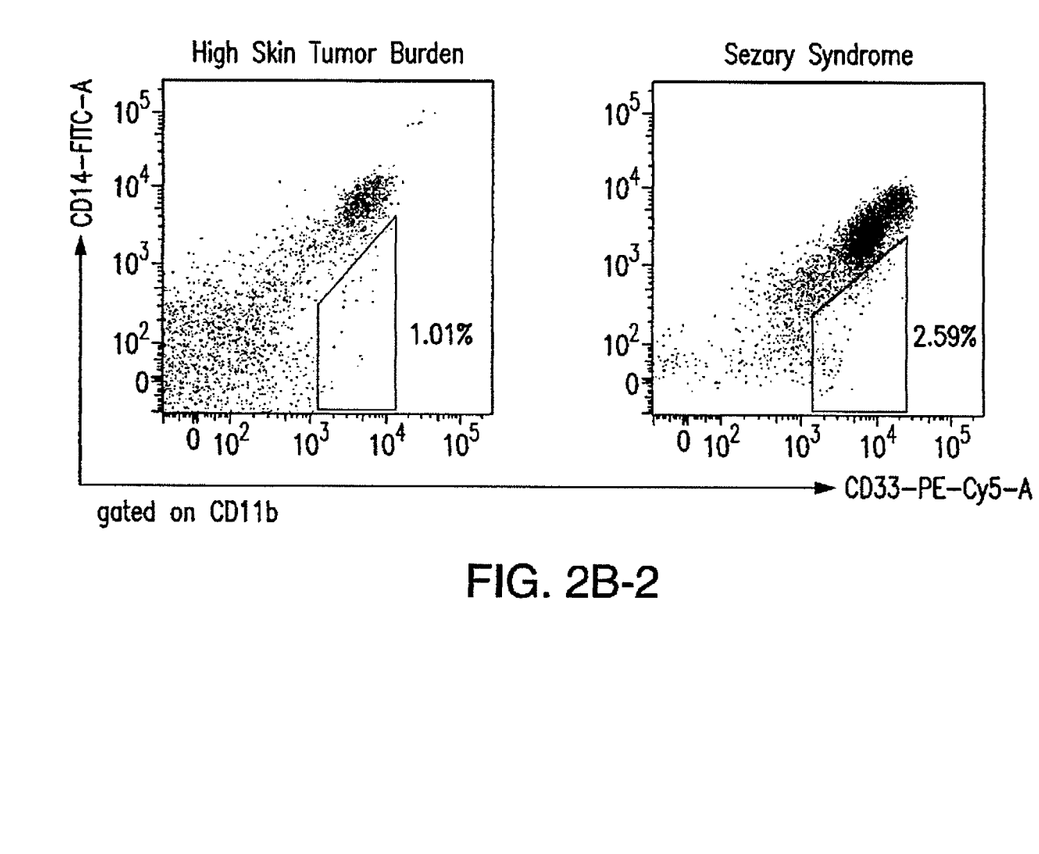
Figure 2C:
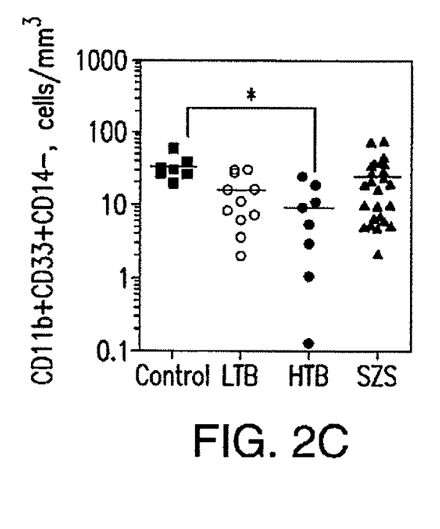
Figure 2D:
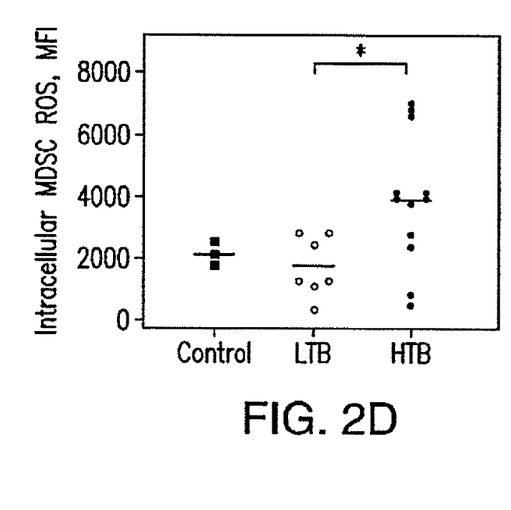
Figure 2E:
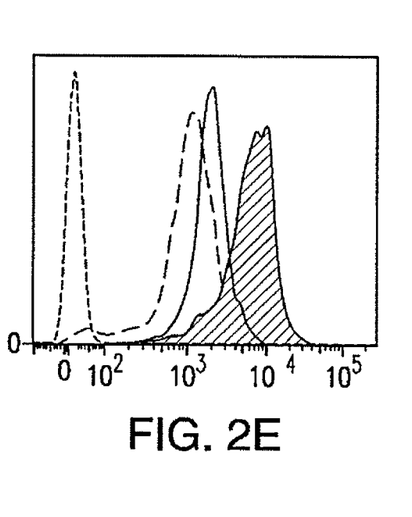
Figure 3A:
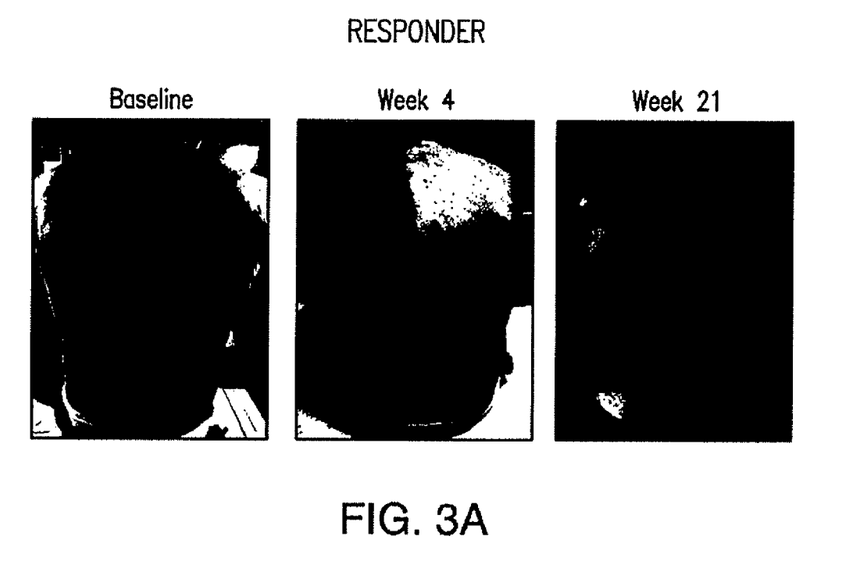
FIGS. 3A-3B. Clinical effect of therapy with IFN-$\alpha_{2b}$ in representative patient with IB of MF (T2N0M0B0) at time of diagnosis improved significantly after 4 injections of IFN-$\alpha_{2b}$ at 150 mcg weekly and continued to improve by time of 21 injections. 3A. Responder baseline, responder after four weeks of IFN-$\alpha_{2b}$ therapy, and responder after twenty-one weeks of IFN-$\alpha_{2b}$ therapy. 3B. Non-responder baseline and non-responder after twenty-one weeks of IFN-$\alpha_{2b}$ therapy.
Figure 3B:
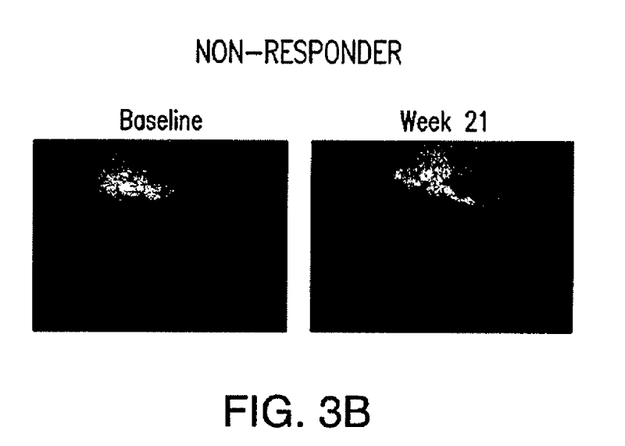

We evaluated human granulocytic MDSC with CD33+ CD11b+CD86+CD14−HLA-DR− phenotype (FIG. 2A). Across the patient population studied, we found that in the peripheral blood the average proportion of CD33+CD14− among CD11b+ cells was 2.5±0.7% in normal volunteers (N=7), 1.4±0.9% in patients in low tumor burden (N=11), 1.0±0.7% in patients with high skin tumor burden (N=8), and 2.6±1.3% in patients with SzS (N=26) (FIG. 2B, representative flow). We found a statistically significant decrease in absolute number of MDSC in patient with HTB ($p<0.05$) (FIG. 2C). These difference was even more pronounced when ratio of MDSC per ANC was established for these patients (FIG. 2D). However, despite of decreasing numbers of MDSC with increased tumor burden, their ROS production was significantly increased proportionally to tumor burden ($p<0.05$) (FIG. 2E-F).

Figure 4A:
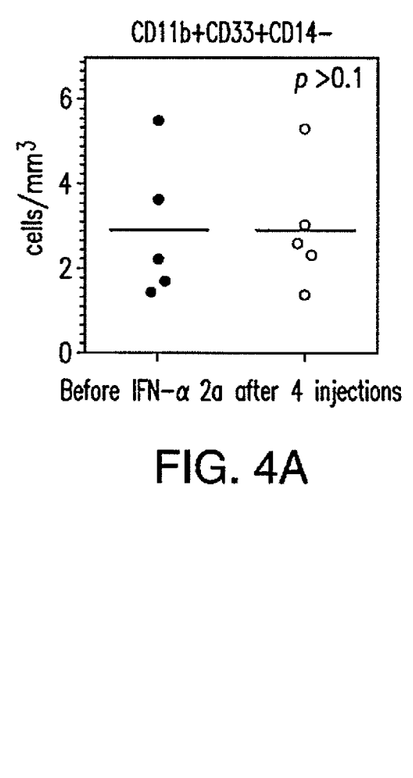
Figure 4B:
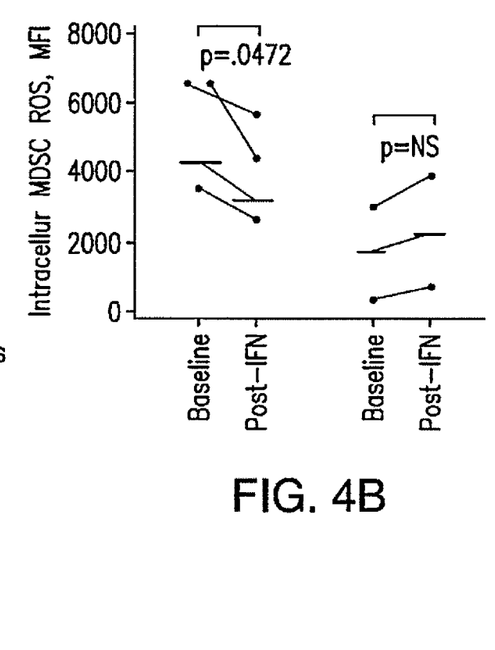
Figure 4C:
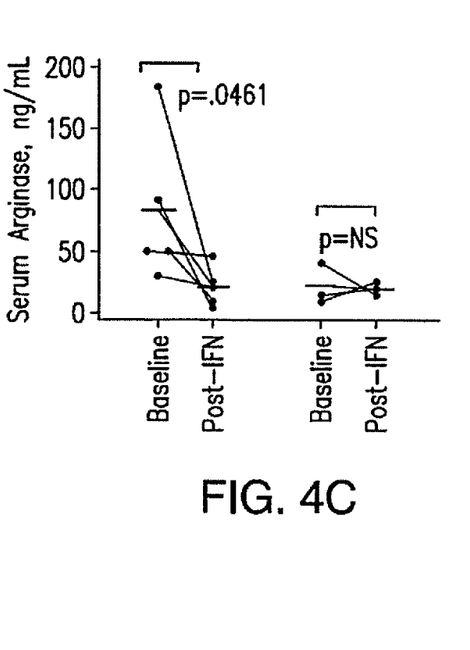

Seven patients were treated weekly with subcutaneous injection of PEG-interferon α2b PEGINTRON®) at 1.25 mcg/kg. MDSC were detected in peripheral blood before the beginning of the therapy and after 4 injections. All patients developed neutropenia after 4 injections of PEGINTRON® (peginterferon α-2b). Percentage of MDSC remained unchanged in patients who benefited from the therapy with PEGINTRON® (peginterferon α-2b) (FIG. 4A) as well as in patients whose disease progressed while being treated with PEGINTRON® (peginterferon α-2b) (data not shown). However, we found that the ROS production by MDSC was reduced significantly in responders ($p<0.05$), while the level of ROS remained unchanged in patient who did not benefit from therapy with PEGINTRON® (peginterferon α-2b) (FIG. 4B). Decrease in ROS production was associated with intracellular pSTAT3 level and serum arginase-1 (FIG. 4C).

Thus, we demonstrated that the benefit of therapy with INF-α2b is mediated in part via reduction of ROS production by MDSC in patients with CTCL rather than decrease in absolute number of MDSC.

6.3 Discussion

An increase in the number of immune-suppressive cells has been correlated with tumor-induced immunosuppression, and depletion of MDSC in tumor models has been associated with tumor-specific immune responses.[7,8] Reduction of immunosuppressive cells in cancer patients could enable reconstitution of mechanisms important for immune surveillance and/or facilitate the induction of tumor-specific immune responses when used as an adjunct for tumor-specific immunotherapy. Here, we sought to evaluate the number and level of activation of MDSC in peripheral blood of CTCL patients and to directly evaluate the effects of IFN-$\alpha_{2b}$ on MDSC in CTCL patients.

In the initial studies, we phenotypically and functionally characterized MDSC populations in CTCL patients across different clinical stages. Our studies suggest that CTCL patients with a high tumor burden have fewer MDSC when compared to normal volunteers, or with patients with low tumor burden.

We demonstrated a decrease in the number of circulating MDSC in patients with advanced MF. One possible explanation for this phenomenon would be a tissue accumulation of MDSC during later stages of the disease. However, lack of specific markers for MDSC makes their study in the skin difficult. Nonetheless, we observed increased activation of MDSC with increasing tumor burden. We used a surrogate marker, the level of ROS produced by MDSC, as a measure of their activation.[9,10] We demonstrated that the intracellular ROS of MDSC was significantly elevated in patients with high skin tumor burden.

REFERENCES

1. Vasievich E A, Huang L: The suppressive tumor microenvironment: a challenge in cancer immunotherapy. Mol Pharm 8:635-41, 2011
2. Cai W, Qin A, Guo P, et al: Clinical significance and functional studies of myeloid-derived suppressor cells in chronic hepatitis C patients. J Clin Immunol 33:798-808, 2013
3. Norris B A, Uebelhoer L S, Nakaya H I, et al: Chronic but not acute virus infection induces sustained expansion of myeloid suppressor cell numbers that inhibit viral-specific T cell immunity. Immunity 38:309-21, 2013
4. Steding C E, Wu S T, Zhang Y, et al: The role of interleukin-12 on modulating myeloid-derived suppressor cells, increasing overall survival and reducing metastasis. Immunology 133:221-38
5. Sinha P, Clements V K, Ostrand-Rosenberg S: Reduction of myeloid-derived suppressor cells and induction of M1 macrophages facilitate the rejection of established metastatic disease. J Immunol 174:636-45, 2005
6. Zoglmeier C, Bauer H, Norenberg D, et al: CpG blocks immunosuppression by myeloid-derived suppressor cells in tumor-bearing mice. Clin Cancer Res 17:1765-75, 2011
7. Le H K, Graham L, Cha E, et al: Gemcitabine directly inhibits myeloid derived suppressor cells in BALB/c mice bearing 4T1 mammary carcinoma and augments expansion of T cells from tumor-bearing mice. Int Immunopharmacol 9:900-9, 2009
8. Poehlein C H, Haley D P, Walker E B, et al: Depletion of tumor-induced Treg prior to reconstitution rescues enhanced priming of tumor-specific, therapeutic effector T cells in lymphopenic hosts. Eur J Immunol 39:3121-33, 2009
9. Youn J I, Gabrilovich D I: The biology of myeloid-derived suppressor cells: the blessing and the curse of morphological and functional heterogeneity. Eur J Immunol 40:2969-75, 2011
10. Corzo C A, Cotter M J, Cheng P, et al: Mechanism regulating reactive oxygen species in tumor-induced myeloid-derived suppressor cells. J Immunol 182:5693-701, 2009

Various publications are cited herein, the contents of which are hereby incorporated by reference in their entireties.

What is claimed is:

1. A method of treating a subject suffering from cutaneous T-cell lymphoma with interferon-α, by comparing activation levels of myeloid-derived suppressor cells in the subject in response to a test dose of interferon-α, said method comprising:

(i) determining a first activation level of myeloid-derived suppressor cells in the subject;
(ii) administering a test dose of interferon-α to the subject;
(iii) determining a second activation level of myeloid-derived suppressor cells in the subject after administering the test dose of interferon-α to the subject;
(iv) comparing the first activation level to the second activation level;
(v) determining that the subject has a greater likelihood of benefiting from an interferon-α treatment when the second activation level is reduced compared to the first activation level; and
(vi) where the second activation level is reduced compared to the first activation level, treating the subject with interferon-α.

2. The method of claim 1 where the subject has not been treated with interferon-α prior to administering the test dose of interferon-α.

3. The method of claim 1 where the test dose of interferon-α is a single test dose.

4. The method of claim 1 where the first and the second activation levels of myeloid-derived suppressor cells are measured via a marker of myeloid-derived suppressor cells activity.

5. The method of claim 4 where the marker is intracellular reactive oxygen species.

6. The method of claim 4 where the marker is serum arginase 1.

7. The method of claim 4 where the marker is intracellular pSTAT3.

* * * * *